(12) United States Patent
Ericson et al.

(10) Patent No.: US 6,456,096 B1
(45) Date of Patent: Sep. 24, 2002

(54) MONOLITHICALLY COMPATIBLE IMPEDANCE MEASUREMENT

(75) Inventors: Milton Nance Ericson, Knoxville; David Eugene Holcomb, Oak Ridge, both of TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/566,764

(22) Filed: May 8, 2000

(51) Int. Cl.[7] .................. G01R 27/08; G01R 27/26; G01R 27/28; G06M 1/10; H01L 29/00
(52) U.S. Cl. ............ 324/707; 324/698; 324/685; 324/686; 324/691; 324/654; 324/76.16; 257/528; 257/540
(58) Field of Search .................. 324/707, 698, 324/681, 670, 674, 684, 685, 686, 691, 76.16, 76.53, 75.52, 76.75, 654, 76.47; 257/528, 531, 536, 540

(56) References Cited

U.S. PATENT DOCUMENTS

| | | | | |
|---|---|---|---|---|
| 3,626,285 A | * | 12/1971 | Hartke | 324/683 |
| 3,778,706 A | | 12/1973 | Thompson | |
| 3,896,374 A | * | 7/1975 | Delafon | 324/681 |
| 4,041,382 A | * | 8/1977 | Washburn | 324/707 |
| 4,150,573 A | * | 4/1979 | Iinuma et al. | 324/707 |
| 4,358,749 A | * | 11/1982 | Clark | 340/941 |
| 4,517,547 A | | 5/1985 | Gray et al. | |
| 4,567,437 A | | 1/1986 | Hubbard | |
| 4,733,556 A | * | 3/1988 | Meitzler et al. | 73/53.05 |
| 5,089,780 A | | 2/1992 | Megerle | 324/448 |
| 5,260,667 A | | 11/1993 | Garcia-Golding et al. | 324/694 |
| 5,274,335 A | | 12/1993 | Wang et al. | 324/689 |
| 5,332,961 A | | 7/1994 | Hammerle | 324/700 |
| 6,057,693 A | | 5/2000 | Murphy et al. | |

FOREIGN PATENT DOCUMENTS

| | | |
|---|---|---|
| FR | 2473626 A | 7/1981 |
| WO | WO 98 27409 A | 6/1998 |
| WO | WO 98 45672 A | 10/1998 |

OTHER PUBLICATIONS

David E. Holcomb, et al., "Transducers for Temperature, Pressure, and Flow," Encyclopedia of Applied Physics, vol. 22, Wiley VCH, pp. 35–65 (1998).

Hang–Sheng Lee, et al., "In situ monitoring of high–temperature degraded engine oil condition with microsensors," Sensors and Actuators B, vol. 20, pp. 49–54 (1994).

(List continued on next page.)

Primary Examiner—N. Le
Assistant Examiner—Anjan K. Deb
(74) Attorney, Agent, or Firm—Akerman, Senterfitt & Edison, P.A.

(57) ABSTRACT

A monolithic sensor includes a reference channel and at least one sensing channel. Each sensing channel has an oscillator and a counter driven by the oscillator. The reference channel and the at least one sensing channel being formed integrally with a substrate and intimately nested with one another on the substrate. Thus, the oscillator and the counter have matched component values and temperature coefficients. A frequency determining component of the sensing oscillator is formed integrally with the substrate and has an impedance parameter which varies with an environmental parameter to be measured by the sensor. A gating control is responsive to an output signal generated by the reference channel, for terminating counting in the at least one sensing channel at an output count, whereby the output count is indicative of the environmental parameter, and successive ones of the output counts are indicative of changes in the environmental parameter.

12 Claims, 1 Drawing Sheet

OTHER PUBLICATIONS

Fernando Garcia–Golding, et al., "Sensor for determining the water content of oil–in–water emulsion by specific admittance measurement," Sensors and Actuators A, vol. 46–47, pp: 337–341 (1995).

George S. Saloka, et al., "A Capacitive Oil Deterioration Sensor," Society of Automotive Engineering, International Congress and Exposition, Detroit, Michigan, pp. 137–146 (Feb. 1991), SAE Technical Paper 910497.

* cited by examiner

MONOLITHICALLY COMPATIBLE IMPEDANCE MEASUREMENT

STATEMENT REGARDING FEDERALLY SPONSORED RESEARCH OR DEVELOPMENT

This Invention was made with government support under contract DE-AC05-96OR22464, awarded by the United States Department of Energy, and the United States Government has certain rights in this invention.

BACKGROUND OF THE INVENTION

1. Field of the Invention

This invention relates generally to the field of remote sensors and sensing, and in particular, to integrated remote sensors and sensing.

2. Description of Related Art

Many problems prevent wide-temperature range impedance measurements in harsh environments. Prior art impedance measurement devices and methods require very high tolerance, very expensive precision voltage or current sources. Precision impedance measurement underpins many sensor readout systems. For example, RTDs, thermistors, and associated measurement schemes. The other common temperature measurement sensor type, thermocouples, also relies upon high-gain temperature-stable amplifiers with minimal input offset and gain errors. These devices and methods are described by David E. Holcomb and Timothy E. McKnight, "Transducers for Temperature, Pressure, and Flow", *Encyclopedia of Applied Physics,* Vol. 22, Wiley-VCH, 1998, pp. 35–65.

Prior art circuits also require temperature stable, high-accuracy time base circuits. Prior art circuits do not directly generate digital data as an output, and are further subject to temperature related errors associated with analog to digital conversion methods. Prior art circuits are not filly monolithically compatible.

Impedance measurement is not limited to temperature measurement and is often required for applications such as oil condition monitoring.

In situ monitoring of high-temperature degraded engine oil condition with micro sensors is described by Hang-Sheng Lee, Simon S. Wang, Donald J. Smolenski, Michael B. Viola, and Edward E. Klusendorf, *Sensors and Actuators B,* Vol. 20, 1994, pp.49–54

A sensor for determining the water content of oil-in-water emulsion by specific admittance measurement is described by Fernando Garcia-Golding, Mario Giallorenzo, Noel Moreno, and Victor Chang, *Sensors and Actuators A,* Vol. 46–47, 1995, pp. 337–341.

U.S. Pat. No. 5,274,335—Wang, et al. describes oil sensor systems and methods of qualitatively determining oil type and condition, 1993.

U.S. Pat. No. 5,089,780—Megerle describes an oil quality monitor sensor and system.

U.S. Pat. No. 4,733,556—Meitzler et al. describes method and apparatus for sensing the condition of lubrication oil in an internal combustion engine.

U.S. Pat. No. 5,332,961—Hammerle describes a resistive oil quality sensor.

A capacitive oil deterioration sensor is described in "A Capacitive Oil Deterioration Sensor", George S. Saloka and Allen H. Meitzler, Society of Automotive Engineering International Congress and Exposition, Detroit Mich., Feb. 25–Mar. 1, 1991, pp. 137–146

U.S. Pat. No. 5,260,667—Garcia-Golding et al. describes a method and apparatus for determining the percentage water content of an oil-in-water emulsion by specific admittance measurement.

Accordingly, there is a long-felt need for simpler, more reliable and less expensive methods and apparatus for wide-temperature range impedance measurements, particularly in remote environments.

SUMMARY OF THE INVENTION

The long-felt need for simpler, more reliable and less expensive methods and apparatus for wide-temperature range impedance measurements, particularly in harsh environments, is satisfied by a new temperature compensated impedance measurement method and apparatus in accordance with the inventive arrangements. The inventive arrangement is applicable to both resistance- and capacitance-based measurements.

Prior approaches to impedance measurement have relied on precision component values and high-accuracy readout electronics. The inventive arrangements employ a new approach, namely tracking the thermal drift of components through thermal matching the entire measurement circuit preferably on a single silicon substrate. Other drifts associated with harsh environments such as pressure and vibration sensitivities are also compensated for by monolithic construction. Monolithic construction also assures minimal component value mismatch as compared to non-monolithic implementation schemes. The result is a breakthrough beyond even the most recent developments in the field. Very small, inexpensive impedance measurement devices in accordance with the inventive arrangements are monolithically compatible and capable of operating over a wide temperature range within very harsh environments. Use in oil well drill bits is a suggested application.

More particularly, the inventive arrangements use two identical oscillator circuits, each having an output frequency dependent on both embedded and sensing devices, the sensing devices being resistive and/or capacitive. Gated counters produce a result that is dependent only on the value of the sensing element. Temperature induced measurement errors are compensated for by controlling the counting window of the sensing oscillator with a fixed-width counter whose counting frequency is dependent only on fixed passive elements with matching temperature coefficients and error sources as the sensing oscillator. Temperature coefficients associated with passive elements, variations in power supply voltages, dc offsets, and other temperature dependencies are eliminated by ratioing the outputs of the two gated counters to produce an output solely dependent on the passive characteristics of the sensor. All passive elements except for the sensor are either temperature stable, or track the corresponding elements in the compensation channel very precisely, as is possible with monolithic construction.

This method, and corresponding apparatus, have several advantages over the prior art, including simplicity, wide temperature range operation, harsh environment tolerance, voltage supply variation tolerance, monolithic compatibility and direct digital output. It is a special advantage that a measuring system in accordance with the inventive arrangements is monolithically compatible, because monolithic sensors can operate at very low power levels making it ideal for portable applications.

Moreover, the temperature stable, precision amplifiers, current sources, voltage sources, and time bases associated with prior art methods are not needed. Temperature stable, precision amplifiers are sensitive to temperature-related gain and input offset errors. A monolithic sensor, in accordance with the inventive arrangements, comprises: a reference channel including a reference oscillator and a reference counter driven by the reference oscillator; at least one sensing channel including a sensing oscillator and a sensing counter driven by the sensing oscillator; a semiconducting substrate, the reference channel and the sensing channels being formed integrally with the substrate and intimately nested with one another on the substrate, the reference channel and the sensing channels thereby having precisely matched component values and temperature coefficients; a frequency determining component of the sensing oscillator formed integrally with the substrate, the frequency determining component having an impedance parameter which varies with an environmental parameter to be measured by the sensor; and a gating control, responsive to an output signal generated by the reference channel, for terminating counting in the sensing channels at an output count, whereby the output count is indicative of the environmental parameter, and successive ones of the output counts are indicative of changes in the environmental parameter.

The output signal generated by the reference channel can be a counter overflow indicator signal. The output signal could also be a programmed counter value.

The frequency determining component can be a capacitor, resistor, or inductor.

The impedance parameter can be capacitance, resistance, or inductance.

One of the terminals of the frequency determining component can be integrally electrically grounded. This can be employed allowing a single wire connection to the sensor.

The sensor can comprise a plurality of the sensor channels coupled to the reference channel and operating in parallel with one another.

The sensor can further comprise a scaler for adjusting the reference and sensing oscillators responsive to an output signal of the sensing counter. The scaler can control a binary weighted resistance switching network. This allows a wide-range impedance measurement.

The reference oscillator and the sensing oscillator can be phase locked to one another and use the phase difference as the indicator of sensor impedance variance.

While monolithic mounting typically is the most convenient technique for component matching, all that is required to match component value drift is to intimately thermally nest the components.

A method for remote sensing, according to the inventive arrangements, comprises the steps of: precisely matching component values and temperature coefficients of a reference counting channel and at least one sensing counting channel by intimately nesting the channels with one another on a semiconductor substrate; integrally forming in the substrate a frequency determining component of the at least one sensing channel, the frequency determining component having an impedance parameter which can vary with an environmental parameter; exposing the substrate to a variable environmental parameter; counting with the reference channel at a predetermined frequency, and at the same time, counting with the at least one sensing channel at a frequency related to the varying environmental parameter; terminating counting of the active sensing channels when the reference channel reaches a predetermined count; and correlating a final count of the at least one sensing channel with the environmental parameter, whereby the variable environmental parameter can be precisely, indirectly measured.

DETAILED DESCRIPTION OF THE PREFERRED EMBODIMENTS

The inventive concepts provide a new methodology, and corresponding apparatus, for isolating and measuring the impedance changes of a sensing element. As an apparatus, the invention is a transducer. When the temperature is not the desired parameter to be measured, the changes can be due to a number of effects including but not limited to non-thermal effects on the transducer, such as dielectric substitution in a capacitive sensor. When temperature is the desired parameter to be measured, the changes can be due to thermal effects on the transducer.

Figure 1:
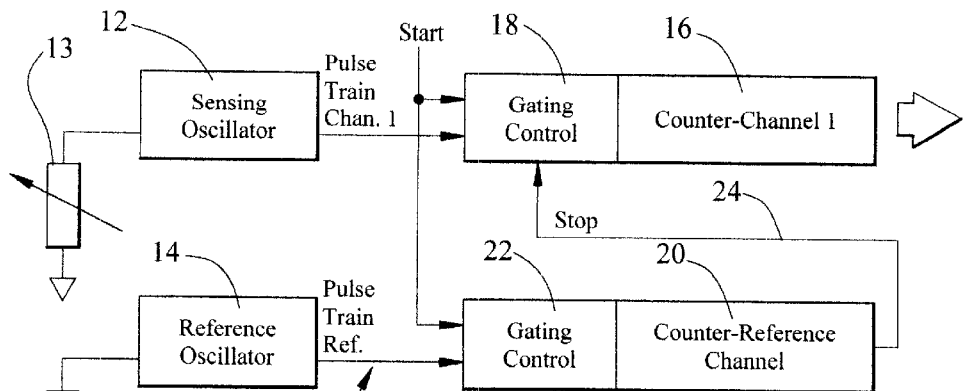
FIG. 1 is a block diagram of an impedance measurement topology in accordance with the inventive arrangements displaying a single measurement channel.

A block diagram of the topology of a transducer embodied as an impedance—to-digital count measurement converter is shown in FIG. 1. The converter 10 comprises a sensing oscillator 12 and a reference oscillator 14, which are intimately nested on the same substrate of a semiconductor, in accordance with the inventive arrangements. Nesting of the components on the same substrate allows precise matching of component values and temperature coefficients, thus providing inherent temperature stability to ratio-dependent measurements employing the oscillators 12 and 14. The frequency of oscillator 12 is controlled by variable capacitor $C_{sens}$. As explained more fully in connection with FIG. 2, a sensing impedance 13, such as capacitor $C_{sens}$, is a frequency determining component of the sensing oscillator 12, formed integrally with the semiconductor substrate. The frequency determining component 13 has an impedance, for example capacitance, resistance, or inductance, which varies with an environmental parameter to be measured by the sensor. The frequency of oscillator 14 is controlled by fixed reference impedance 15, such as capacitor $C_{ref}$, which corresponds to the type of impedance used for the frequency determining component 13.

A pulse train generated by oscillator 12, and designated as Channel 1 pulse train, is an input to a sensing counter 16, designated as Channel 1 counter. The input to the counter 16 is controlled by a gating control 18. A pulse train generated by oscillator 14, and designated as reference pulse train, is an input to a counter 20, designated as Reference Channel counter. The input to the counter 20 is controlled by a gating control 22. The inputs to the gating control 18 are the Channel 1 pulse train and an externally generated start signal. The inputs to the gating control 22 are the reference pulse train and the externally generated start signal. The output signal from the reference channel counter 20 is applied by conductor 24 to a control input for the gating control 18. When the reference oscillator 14 causes counter 20 to overflow or reach a programmed count, the Channel 1 sensing counter 16 is stopped. Gating control 18 will supply the Channel 1 pulse train to the input of the counter 16 provided that the start signal is present, or has been detected, and provided that the counter 20 has not overflowed. Gating control 22 will supply the reference pulse train to the input of the counter 20 provided that the start signal is present, or has been detected. Various logical gate configurations can be used for these functions. The start signal can be a pulse that also resets or initializes the detector, and thereafter, initiates or enables counting.

Figure 2:
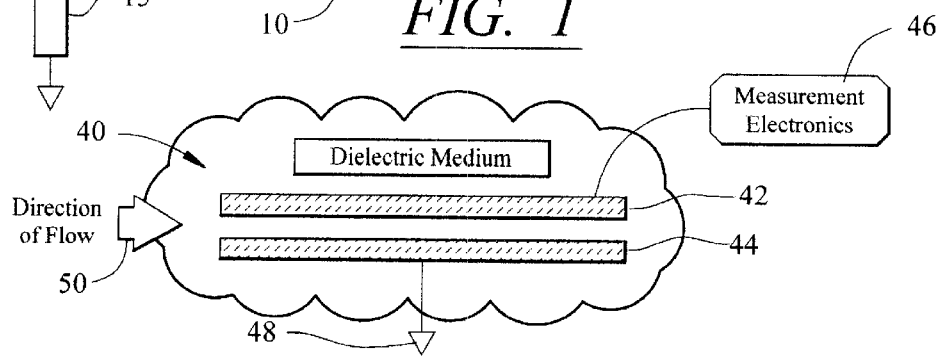
FIG. 2 is a diagram of a sensor measuring dielectric variance of a flow in accordance with the inventive arrangements.

A frequency determining component 13 for the sensing oscillator 12 is shown in FIG. 2. The frequency determining component is embodied as a capacitor. The impedance parameter which is measured is the dielectric variation of the sensing capacitor. In the illustrated example, it is desired to measure the dielectric constant of the media within the capacitive sensor independently of temperature variation. The sensor 40 forms a dielectric medium and has two capacitive "plates" 42 and 44. Measurement electronics 46 are formed integrally with the substrate adjacent plate 42. Plate 44 is grounded, as indicated by ground 48. The direction of dielectric medium flow is as indicated by arrow 50. Alternatively, the frequency-determining component can be a variable resistor or inductor, such as an RTD. As a further alternative, multiple variable frequency determining components of both types can be utilized.

The frequency of the reference oscillator is given by Equation 1, $$f = \frac{1}{\alpha R_{ref} C_{ref}} \quad (1)$$

where $\alpha$ is a fixed circuit timing constant, approximately 2.3 in practice. $R_{ref}$ is the reference resistor value, and $C_{ref}$ is the reference capacitor value.

Correspondingly, the time to reference counter overflow (or reaching programmed value), that is the measurement time $t_{meas}$, can be determined by Equation 2, $$t_{meas} = n\alpha R_{ref} C_{ref} \quad (2)$$

where n is the number of counts to overflow (or reach the programmed value) the reference counter, for example 1024. The term $t_{meas}$ can also be expressed based on the measurement channel, as in Equation 3, $$t_{meas} = counts \alpha R_{sens} C_{sens} \quad (3)$$

where counts is the number of counts in the measurement channel when the reference channel overflows, $R_{sens}$ is the measurement channel resistance and $C_{sens}$ is the sensor capacitance.

Combining equations 2 and 3 yields Equation 4, $$\frac{n}{counts} = \frac{R_{sens} C_{sens}}{R_{ref} C_{ref}}. \quad (4)$$

Since $\gamma = R_{ref}/R_{sens}$ does not vary with temperature due to component matching, the determination of counts can be simplified as in Equation 5, $$counts = \gamma n \frac{C_{ref}}{C_{sens}}. \quad (5)$$

$C_{ref}$ is selected in advance to have the same variance in capacitance with temperature as does $C_{sens}$. This requires advance testing of the dielectric media capacitance variance with temperature to allow component matching. This can also be accomplished by employing a reference capacitor containing a known "good" sample of the dielectric media being measured.

Counts will remain constant if $C_{ref}(T)/C_{sens}(T)$ remains constant. Without contamination, that is without dielectric change, $C_{ref}(T)/C_{sens}(T)$ will remain constant due to component matching. With contamination, counts will change directly with increasing contamination, that is with increasing dielectric change, providing the measurement of the desired property.

Another illustrative example of the usefulness of the technique is temperature measurement using a resistive temperature transducer. In this case, counts is determined by Equation 6, $$counts = \beta n \frac{R_{ref}}{R_{sens}} \quad (6)$$

where $\beta$ is the constant ratio of reference to sensing capacitance made possible through thermal response matching of the two capacitors. Thermal matching is easily accomplished through intimately nesting the capacitors on the same substrate. In this case, counts will vary with the ratio of $C_{ref} R_{ref}(T)/R_{sens}(T)$. Both $R_{ref}(T)$ and $R_{sens}(T)$ can have well known functional forms with different quasi-linear variations with temperature, for example an aluminum film resistor on-chip and a platinum film sensing element. This allows establishing a unique relationship between the resistance ratio and temperature.

Figure 3:
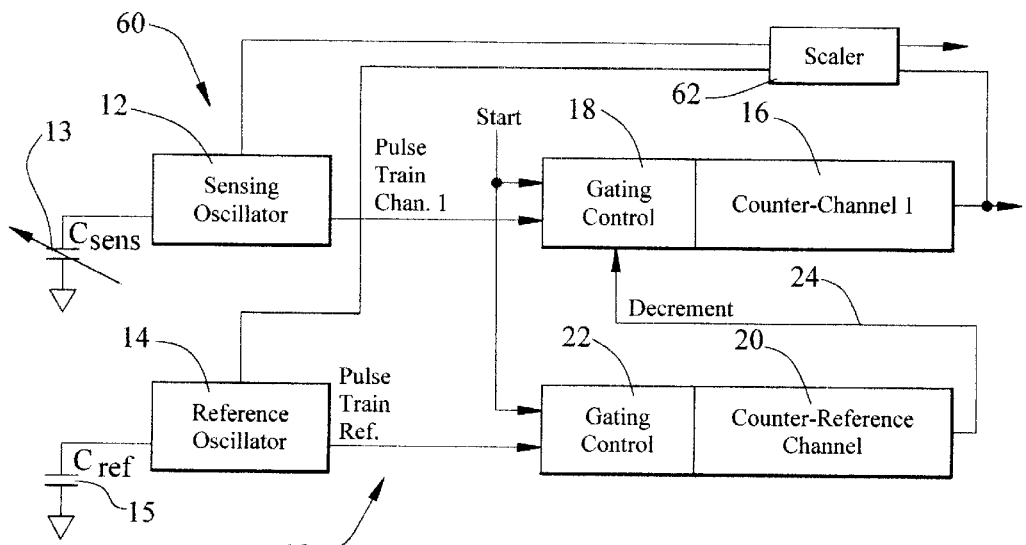
FIG. 3 is a block diagram of an autotuning impedance measurement monitor topology in accordance with the inventive arrangements.

An alternative embodiment in which a scaler is connected to the output of the sensing counter is shown in FIG. 3. The converter 60 comprises the sensing oscillator 12, the reference oscillator 14, adjustable capacitor $C_{sens}$, capacitor $C_{ref}$, the sensing counter 16, the gating control 18, the counter 20 and the gating control 22. As in FIG. 1, when the reference oscillator 14 causes counter 20 to overflow (or reach programmed value), the Channel 1 sensing counter 16 is stopped. The scaler 62 generates signals for controlling the oscillators in the reference and sensing channel, and receives the output signal of the reference channel as an input. The scaler can be used to switch additional impedance into either the reference or sensing oscillators to adjust the oscillator frequency. Adjustments can be made so that the frequencies remain close, yielding maximum measurement sensitivity.

The system is advantageously applicable to parallel use. A plurality of sensor channels can be hooked up to a single reference channel allowing the measurement of several different impedances simultaneously with only one device.

The scaler can also be implemented in such a way that the proper impedance is switched in to match the frequency of the two oscillators, for example implemented as a binary weighted resistance switching network. The binary code required to match the frequencies is the measurement result. Another version can phase lock the frequencies using a voltage-controlled impedance. This voltage, which can be set by a digital-to-analog converter, provides the output.

This invention can be used, for example, to monitor the status of a lubricant system within roller-cone drill bits to determine, for example, if the seals have failed and/or is contamination present. The sensor can also be used, for example, to measure temperature within the journal bearing of the drill bits to monitor the heating of the bearing with wear.

The invention is also useful for remote temperature measurements in harsh conditions, for example, inside of munitions as a long term fire monitor, immersed in a food processing system to measure time-temperature (e.g., an electric potato wedge), as an automotive brake temperature monitor, industrial exhaust gas or discharge monitor, or tire temperature monitor.

The invention is generally applicable to the field of harsh environment impedance monitoring. This is of particular value in remote lubricated devices such as oil field drill bits or automotive or aircraft lubricant condition monitoring.

What is claimed is:

1. A monolithic temperature compensated sensor, comprising:

a reference channel including a reference oscillator, said reference oscillator including at least one circuit element, and a reference counter driven by the reference oscillator;

at least one sensing channel including a sensing oscillator, said sensing oscillator including at least one sensing element, and a sensing counter driven by the sensing oscillator, said sensing counter providing a digital output, said digital output being a function of a ratio of said reference element to said sensing element; and a semiconductor substrate, said reference channel and said sensing channel being formed integrally with said semiconductor substrate and located substantially adjacent to one another;

wherein said digital output is temperature compensated due to thermal matching resulting from said substantially adjacent positioning of said reference and sensing channels.

2. The sensor of claim 1, wherein said reference counter has a maximum capacity, an overflow of said reference counter occurring upon its count exceeding said maximum capacity, said digital output evaluated when said reference counter overflows.

3. The sensor of claim 1, wherein said sensing element and said reference element each comprise at least one capacitor, said digital output reflecting a value of said sensing capacitor.

4. The sensor of claim 1, wherein said sensing element and said reference element each comprise at least one resistor, said digital output reflecting a value of said sensing resistor.

5. The sensor of claim 1, wherein said sensing element and said reference element each comprise at least one inductor, said digital output reflecting a value of said sensing inductor.

6. The sensor of claim 1, wherein at least one terminal of said sensor is electrically grounded.

7. The sensor of claim 1, wherein said sensor includes a plurality of sensing channels, said sensing channels each using said reference channel and operating in parallel with one another.

8. The sensor of claim 1, further comprising a scaler for adjusting the reference and sensing oscillators responsive to said output signal of the sensing counter.

9. The sensor of claim 8, wherein the scaler controls a binary weighted resistance switching network.

10. The sensor of claim 1, wherein the reference oscillator and the sensing oscillator are phase locked to one another.

11. A method for temperature compensated sensing, comprising the steps of:

providing a sensor including a reference channel and at least one sensing channel, said reference channel including a reference oscillator, said reference oscillator including at least one reference element, and a reference counter driven by said reference oscillator;

said sensing counter including a sensing oscillator, said sensing oscillator including at least one sensing element, said sensing channel providing a digital output, said digital output being a function of a ratio of said reference element to said sensing element, said reference channel and said sensing channel integrally formed with a common semiconductor substrate and located substantially adjacent to one another; and measuring said digital output, wherein said digital output is temperature compensated due to thermal matching resulting from said substantially adjacent positioning of said reference and sensing channels.

12. The method of claim 11, wherein said reference counter has a maximum capacity, further comprising the step of triggering said measuring step upon an overflow of said reference counter, said overflow occurring when its count exceeds said maximum capacity.

* * * * *